US00PP23282P2

(12) United States Plant Patent
Michalik

(10) Patent No.: US PP23,282 P2
(45) Date of Patent: Dec. 25, 2012

(54) ***PETUNIA* PLANT NAMED 'PACTOYEL'**

(50) Latin Name: *Petunia×hybrida*
Varietal Denomination: Pactoyel

(75) Inventor: Andrea Michalik, Dresden (DE)

(73) Assignee: Elsner PAC Jungplanzen GbR, Dresden (DE)

( * ) Notice: Subject to any disclaimer, the term of this patent is extended or adjusted under 35 U.S.C. 154(b) by 0 days.

(21) Appl. No.: 13/135,321

(22) Filed: Jun. 30, 2011

(51) Int. Cl.
*A01H 5/00* (2006.01)

(52) U.S. Cl. ..... Plt./356.1
(58) Field of Classification Search ..... Plt./356.1, Plt./356
See application file for complete search history.

*Primary Examiner* — Annette Para
(74) *Attorney, Agent, or Firm* — C. A. Whealy

(57) ABSTRACT

A new and distinct cultivar of *Petunia* plant named 'Pactoyel', characterized by its upright and mounding plant habit; moderately vigorous growth habit; freely branching habit; early and freely flowering habit; cream-colored flowers with yellow to yellow green-colored centers; overall, the flower color appears dark yellow towards the center and brighter greenish yellow towards the margins; resistance to Mildew; and good garden performance.

1 Drawing Sheet

Botanical designation: *Petunia×hybrida*.
Cultivar denomination: 'PACTOYEL'.

BACKGROUND OF THE INVENTION

The present invention relates to a new and distinct cultivar of *Petunia* plant, botanically known as *Petunia×hybrida* and hereinafter referred to by the name 'Pactoyel'.

The new *Petunia* plant is a product of a planned breeding program conducted by the Inventor in Dresden, Germany. The objective of the breeding program is to create new uniform *Petunia* plants with freely flowering habit, attractive flower coloration and resistance to Mildew.

The new *Petunia* plant originated from a cross-pollination made by the Inventor during the summer of 2006 of two unnamed proprietary selections of *Petunia×hybrida*. The new *Petunia* plant was discovered and selected by the Inventor as a single flowering plant within the progeny of the stated cross-pollination in a controlled environment in Dresden, Germany during the spring of 2007.

Asexual reproduction of the new *Petunia* plant by terminal cuttings in a controlled environment in Dresden, Germany since the autumn of 2007, has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environment such as temperature, daylength and light intensity without, however, any variance in genotype.

The following traits have been repeatedly observed and are determined to be the unique characteristics of 'Pactoyel'. These characteristics in combination distinguish 'Pactoyel' as a new and distinct *Petunia* plant:

1. Upright and mounding plant habit.
2. Moderately vigorous growth habit.
3. Freely branching habit.

4. Early and freely flowering habit.
5. Cream-colored flowers with yellow to yellow green-colored centers; overall, the flower color appears dark yellow towards the center and brighter greenish yellow towards the margins.
6. Resistance to Mildew.
7. Good garden performance.

Plants of the new *Petunia* can be compared to plants of the parent selections. Plants of the new *Petunia* differ primarily from plants of the parent selections in uniformity, flowering habit and flower color.

Plants of the new *Petunia* can also be compared to plants of the *Petunia* 'Veranda Yellow', not patented. In side-by-side comparisons conducted in Dresden, Germany, plants of the new *Petunia* and 'Veranda Yellow' differed primarily in the following characteristics:

1. Plants of the new *Petunia* had smaller flowers than plants of 'Veranda Yellow'.
2. Plants of the new *Petunia* flowered earlier than plants of 'Veranda Yellow'.
3. Plants of the new *Petunia* and 'Veranda Yellow' differed slightly in flower color.
4. Plants of the new *Petunia* were resistant to Mildew whereas plants of 'Veranda Yellow' were susceptible to Mildew.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Pactoyel' grown in a container.

The photograph at the bottom of the sheet is a close-up view of a typical flower of 'Pactoyel'.

DETAILED BOTANICAL DESCRIPTION

The aforementioned photographs and following observations, measurements and values describe plants grown during the spring in 13-cm containers in a glass-covered greenhouse in Dresden, Germany and under commercial practices. During the production of the plants, day temperatures averaged 18° C., night temperatures averaged 16° C. and light levels ranged from 15 to 90 klux. Plants were pinched two times and were four months old when the photographs and description were taken. In the following description, color references are made to The Royal Horticultural Society Colour Chart, 1995 Edition, except where general terms of ordinary dictionary significance are used.

Botanical classification: *Petunia×hybrida* 'Pactoyel'.

Parentage:

*Female, or seed, parent*.—Unnamed proprietary selection of *Petunia×hybrida*, not patented.

*Male, or pollen, parent*.—Unnamed proprietary selection of *Petunia×hybrida*, not patented.

Propagation:

*Type*.—By terminal cuttings.

*Time to initiate roots, summer*.—About seven days at temperatures of 18° C. to 20° C.

*Time to initiate roots, winter*.—About seven to nine days at temperatures of 18° C. to 20° C.

*Time to produce a rooted young plant, summer*.—About three weeks at temperatures of 18° C. to 20° C.

*Time to produce a rooted young plant, winter*.—About three to four weeks at temperatures of 18° C. to 20° C.

*Root description*.—Fibrous; medium in thickness; white in color.

*Rooting habit*.—Freely branching, dense.

Plant description:

*Plant and growth habit*.—Upright and mounding plant habit; freely branching habit with about eight to ten lateral branches developing per plant; pinching enhances lateral branch development; moderately vigorous growth habit.

*Plant height*.—About 28 cm.

*Plant diameter*.—About 35 cm.

Lateral branch description:

*Length*.—About 13 cm to 18 cm.

*Diameter*.—About 3 mm to 4 mm.

*Internode length*.—About 1 cm to 2 cm.

*Strength*.—Moderately strong, flexible.

*Aspect*.—Upright to outwardly spreading.

*Texture*.—Pubescent.

*Color*.—Close to 144A.

Foliage description:

*Arrangement*.—Alternate and opposite, simple.

*Length*.—About 2 cm to 5 cm.

*Width*.—About 1 cm to 3 cm.

*Shape*.—Elliptic.

*Apex*.—Acute.

*Base*.—Attenuate.

*Margin*.—Entire.

*Texture, upper and lower surfaces*.—Pubescent, viscid.

*Venation pattern*.—Pinnate; reticulate.

*Color*.—Developing leaves, upper surface: Close to 146A. Developing leaves, lower surface: Close to 146B. Fully expanding leaves, upper surface: Close to 147A; venation, close to 144A. Fully expanding leaves, lower surface: Close to 147B; venation, close to 144A.

*Petioles*.—Length: About 5 mm to 15 mm. Diameter: About 2 mm. Texture, upper and lower surfaces: Pubescent, viscid. Color, upper and lower surfaces: Close to 144A.

Flower description:

*Flower arrangement and habit*.—Single salverform flowers arising from upper leaf axils; freely flowering habit; flowers face upright to outwardly.

*Fragrance*.—None detected.

*Natural flowering season*.—Early flowering habit, plants of the new *Petunia* begin flowering about six weeks after planting; long flowering period; flowering commences naturally during the spring and plants flower continuously throughout the summer and autumn until frost in Germany.

*Flower longevity*.—Individual flowers last about five to six days on the plant; flowers persistent.

*Flower buds*.—Shape: Tubular. Length: About 3 cm to 4.5 cm. Diameter: About 5 mm to 10 mm. Color: Close to 151B.

*Flower diameter*.—About 4.5 cm to 5 cm.

*Flower length (depth)*.—About 5 cm.

*Throat diameter*.—About 1 cm.

*Tube diameter, base*.—About 2 mm.

*Tube length*.—About 2.5 cm to 3 cm.

*Corolla*.—Arrangement: Five petals fused at the base and opening into a flared trumpet. Petal length from throat: About 2 cm to 2.5 cm. Petal width: About 2 cm to 2.5 cm. Petal shape: Roughly spatulate, rounded. Petal apex: Rounded. Petal margin: Slightly dentate; fringed appearance. Petal texture, upper and lower surfaces: Smooth, glabrous. Throat texture: Smooth, glabrous. Tube texture: Smooth, glabrous. Color: Petal, when opening, upper surface: Close to 151B; towards the margins, close to 157C. Petal, when opening, lower surface: Close to 145B; towards the margins, close to 157C. Petal, fully opened, upper surface: Close to 151B; towards the margins, close to 157B; venation, close to 144B. Petal, fully opened, lower surface: Close to 145B; towards the margins, close to 157B; venation, close to 144B. Throat: Close to 151A; venation, close to 144B. Tube: Close to 151A; venation, close to 144B.

*Calyx*.—Arrangement: One star-shaped calyx with five sepals fused at the base per flower. Sepal length: About 1 cm to 2 cm. Sepal width: About 1 mm to 3 mm. Sepal shape: Oblong. Sepal apex: Obtuse, slightly acute. Sepal margin: Entire. Sepal texture, upper and lower surfaces: Pubescent; viscid. Color, upper surface: Close to 146A. Color, lower surface: Close to 146B.

*Peduncles*.—Length: About 3 cm to 4.5 cm. Diameter: About 1 mm to 2 mm. Aspect: About 25° to 40° from vertical. Strength: Moderately strong. Texture: Pubescent; viscid. Color: Close to 146B.

*Reproductive organs*.—Stamens: Quantity/arrangement: Five per flower. Anther shape: Reniform. Anther length: About 1 mm to 2 mm. Anther color: Close to 2D. Pollen amount: Moderate to abundant. Pollen color: Close to 2D. Pistils: Quantity: One per flower. Style length: About 2 cm to 2.5 cm. Style color: Close to 155B. Stigma shape: Rounded, parted.

Stigma color: Close to 146A. Ovary color: Close to 144B. Seeds and fruits: Seed and fruit development have not been observed on plants of the new *Petunia*.

Garden performance: Plants of the new *Petunia* have been observed to have good garden performance and to tolerate rain, wind and temperatures ranging from about 1° C. to about 35° C. to 40° C.

Pathogen/pest resistance: Plants of the new *Petunia* have been observed to be resistant to Mildew. Plants of the new *Petunia* have not been observed to be resistant to pests and other pathogens common to *Petunia* plants.

It is claimed:

1. A new and distinct *Petunia* plant named 'Pactoyel' as illustrated and described.

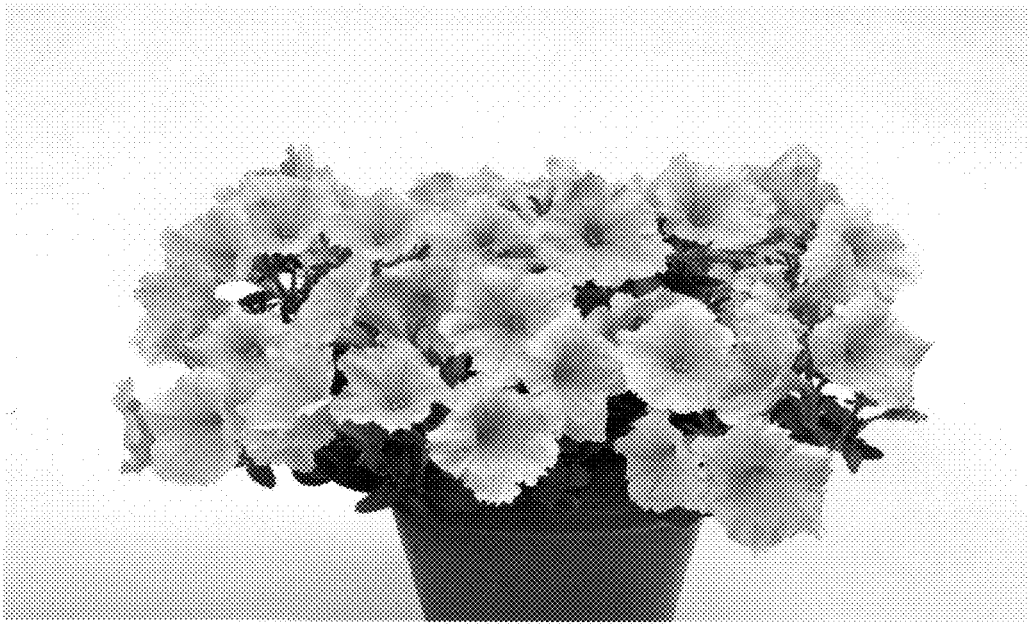
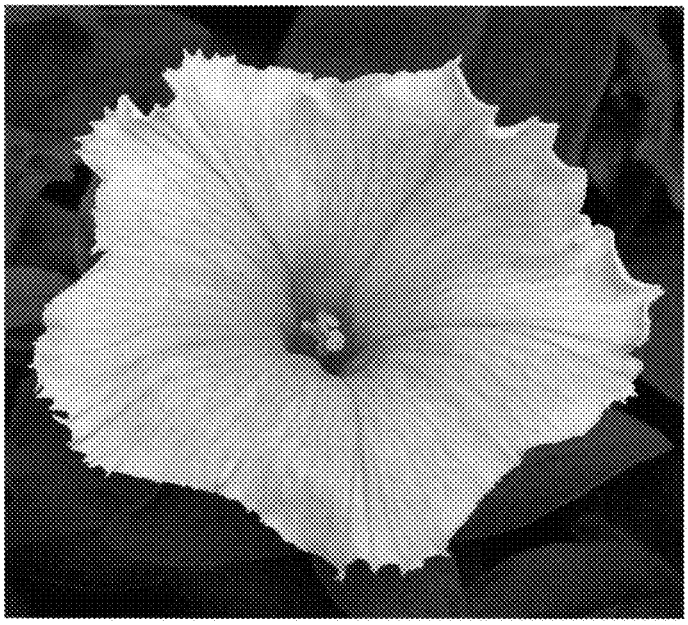

* * * * *